(12) United States Patent
Wiesel

(10) Patent No.: US 7,020,514 B1
(45) Date of Patent: Mar. 28, 2006

(54) METHOD OF AND APPARATUS FOR DETECTING ATRIAL FIBRILLATION

(76) Inventor: Joseph Wiesel, 484 Duryea Ter., W. Hempstead, NY (US) 11552

( * ) Notice: Subject to any disclaimer, the term of this patent is extended or adjusted under 35 U.S.C. 154(b) by 589 days.

(21) Appl. No.: 10/305,691

(22) Filed: Nov. 27, 2002

Related U.S. Application Data

(63) Continuation-in-part of application No. 09/467,233, filed on Dec. 20, 1999, now Pat. No. 6,519,490.

(51) Int. Cl.
*A61B 5/04* (2006.01)

(52) U.S. Cl. .................. 600/518; 600/508; 600/515

(58) Field of Classification Search ............... 600/484, 600/485, 518, 502, 519, 489, 490, 492, 526, 600/508; 607/6, 10
See application file for complete search history.

(56) References Cited

U.S. PATENT DOCUMENTS

| | | | |
|---|---|---|---|
| 3,776,221 A * | 12/1973 | McIntyre ................. 600/485 |
| 4,260,951 A | 4/1981 | Lewyn |
| 4,262,674 A * | 4/1981 | Uemura et al. ............ 600/493 |
| 4,524,777 A * | 6/1985 | Kisioka et al. ............ 600/490 |
| 4,621,643 A | 11/1986 | New, Jr. et al. |
| 4,685,464 A | 8/1987 | Goldberger et al. |
| 4,700,708 A | 10/1987 | New, Jr. et al. |
| 5,113,869 A | 5/1992 | Nappholz et al. |
| 5,117,834 A | 6/1992 | Kroll et al. |
| 5,228,449 A | 7/1993 | Christ et al. |
| 5,342,404 A | 8/1994 | Alt et al. |
| 5,456,261 A | 10/1995 | Luczyk |
| 5,464,431 A * | 11/1995 | Adams et al. ................. 607/4 |
| 5,464,434 A * | 11/1995 | Alt ................................. 607/6 |
| 5,471,991 A | 12/1995 | Shinnar |
| 5,609,158 A | 3/1997 | Chan |
| 5,626,143 A | 5/1997 | Meyer, III |
| 5,772,604 A | 6/1998 | Langberg et al. |
| 5,776,071 A * | 7/1998 | Inukai et al. ............... 600/493 |
| 5,817,134 A * | 10/1998 | Greenhut et al. ............ 607/14 |
| 5,842,997 A | 12/1998 | Verrier et al. |
| 5,865,756 A * | 2/1999 | Peel, III ..................... 600/490 |
| 5,941,831 A * | 8/1999 | Turcott ....................... 600/515 |

(Continued)

OTHER PUBLICATIONS

International Search Report for PCT/US02/18044 Joseph Wiesel filed Jun. 6, 2002.

(Continued)

*Primary Examiner*—Robert E. Pezzuto
*Assistant Examiner*—Brian T. Gedeon
(74) *Attorney, Agent, or Firm*—Gibbons, Del Deo, Dolan, Griffinger & Vecchione

(57) ABSTRACT

A method and apparatus to determine possible atrial fibrillation that includes detecting irregular pulse rhythms from a succession of time intervals each corresponding to a respective interval of time between successive pulse beats of a sequence of the pulse beats; analyzing the detected irregular pulse rhythms to make a determination of possible atrial fibrillation; indicating the possible atrial fibrillation from the determination. If a sphygmomanometer is used, a plurality of pulse beats may be detected with it including the sequence of pulse beats; and respiratory variation in systolic pressure of the pulse beats may be compensated by designating the succession of time intervals to exclude at least an initial one of the plurality of time intervals.

22 Claims, 2 Drawing Sheets

U.S. PATENT DOCUMENTS

| | | | |
|---|---|---|---|
| 6,017,313 A * | 1/2000 | Bratteli et al. | 600/485 |
| 6,064,906 A * | 5/2000 | Langberg et al. | 600/518 |
| 6,095,984 A | 8/2000 | Amano et al. | |
| 6,126,595 A | 10/2000 | Amano et al. | |
| 6,249,700 B1 | 6/2001 | Alt | |
| 6,327,499 B1 | 12/2001 | Alt | |
| 6,423,010 B1 * | 7/2002 | Friedman et al. | 600/494 |

OTHER PUBLICATIONS

Bert K. Bootsma et al Analysis of R-R Intervals in Patients With Atrial Fibrillation at Rest and During Exercise. Dept. of Cardiology, University Hospital, The Netherlands—vol. XLI—May 1970.

Jospeh Wiesel et al "The Use of a Modified Sphygmomanometer to Detect Atrial Fibrillation in Outpatients", PACE, vol. 27 (May 2004).

Brunswald's A Textbook of Cardiovascular Medicine, 7th Edition, 2005, pp. 817, 840.

Degown's Diagnostic Examination, 8th Edition, 2004, p. 362.

* cited by examiner

METHOD OF AND APPARATUS FOR DETECTING ATRIAL FIBRILLATION

CROSS-REFERENCE TO COPENDING PATENT APPLICATIONS

This is a continuation-in-part of Ser. No. 09/467,233, filed Dec. 20, 1999, now U.S. Pat. No. 6,519,490.

BACKGROUND OF THE INVENTION

1. Field of the Invention

The present invention generally relates to a method of and an apparatus for detecting atrial fibrillation by monitoring and analyzing pulse beats.

2. Discussion of the Related Art

The heart is the major muscle that functions as the primary pump for blood flow throughout the body. The heart contains two upper chambers called atria and two lower chambers called ventricles. The right atrium receives oxygen-depleted blood while the left atrium receives blood enriched with oxygen from the lungs. When the atria are full, the outlet valves within the heart open and the atria squeeze blood into the ventricles. The right ventricle then pumps oxygen-depleted blood to the lungs while the left ventricle pumps oxygen-enriched blood to all parts of the body. In this fashion, the heart functions primarily as a double sided pump.

The heart's internal pacemaker, known as the sinus node, signals the start of each heart beat. This signal originates in the right atrium in the sinoatrial node and travels simultaneously to the left atrium and down to the interatrial septum to the atrioventricular node. The cycle of electrical stimulation that normally occurs is referred to as normal sinus rhythm. The contraction of the ventricles will be referred to as the heart beats.

Many rhythm abnormalities may be present. Atrial fibrillation is one rhythm abnormality in which the atria do not contract normally. Instead, there is a continuously varying pattern of electrical activation of the atria resulting in a rapid highly irregular pattern of impulses reaching the atrioventricular node. The atrioventricular node acts as a filter and allows a reduced number of these impulses to reach the ventricles which results in a highly irregular heartbeat pattern. This irregular pattern has been shown in previous studies to be a random pattern (Bootmsma et al: Analysis of R—R Intervals in Patients with Atrial Fibrillation at Rest and During Exercise. Circulation 41: 783, 1970). Whenever the term "irregular" is used in this application it refers to this random pattern of beats found almost exclusively in atrial fibrillation.

Atrial fibrillation is one of the most common arrhythmias requiring medical attention. Atrial fibrillation may be caused by a number of heart conditions, such as angina, myocardial infarction, heart valve abnormalities, and high blood pressure. These conditions may stretch or scar the atria, thereby causing irregularities in the heart system. Atrial fibrillation may also accompany lung problems or thyroid gland disorders and is also associated with significant morbidity and possible mortality. All persons, young and old, female or male, including the visually and/or sight impaired, may experience atrial fibrillation.

Atrial fibrillation may occur intermittently or chronically. The most serious complication of atrial fibrillation is formation of a blood clot in the left atrium which may result in a stroke. Many people who develop atrial fibrillation, however, are unaware of their abnormal rhythm. Some in the medical profession have, therefore, advocated self screening of the pulse to detect for the possible occurrence of atrial fibrillation. The literature, however, is generally limited to disclosing instructions for manually taking one's pulse accompanied with additional descriptive information.

The reason for using the pulse to detect atrial fibrillation is that the pulse usually corresponds to the heartbeat. The contraction of the left ventricle ejects blood from the heart into the aorta and the resulting pressure wave is detected as a pulse in the arterial system. However, when atrial fibrillation is present, the amount of time between beats varies irregularly.

With a longer time interval between beats, there is more time to fill the ventricles with blood and more blood is ejected by the ventricle in the beat following this long interval. This larger volume of blood in the aorta results in a higher systolic pressure for that beat.

Conversely, when the time interval between beats is short, there is less time for ventricular filling and the volume of blood ejected in the beat following the short time interval is less. This results in a lower systolic pressure for that beat. In some cases, the time interval between beats is so short that the systolic pressure of the following beat is so low that it cannot be palpated as a pulse. A ventricular contraction that cannot be palpated as a pulse in the arterial system results in what is called a "pulse deficit." This is very common in atrial fibrillation. This pulse deficit means that an irregular pattern of heartbeats in the ventricle may result in a less irregular pulse beat pattern since the shortest intervals between heartbeats may not be detected in the pulse. Therefore, any method used to determine the presence of atrial fibrillation by analyzing the time intervals between beats in the ventricles may not be valid when applied to the pulse beats.

An article by Bert K. Bootsma, Adriann J. Hoelen, Jan Strackee and Frits L. Meijler, entitled Analysis of R—R Intervals in Patients with Atrial Fibrillation at Rest and During Exercise, Circulation, Volume XLI, May 1970 describes an analysis of the time intervals between ventricular contractions using the electrocardiogram. The article evaluates the standard deviation divided by the mean of the time intervals between ventricular beats in normal subjects and in those with atrial fibrillation. The article finds that atrial fibrillation can be accurately differentiated from normal sinus rhythm using this formula. However, this was based on ventricular contractions determined by the electrocardiogram and was not applied to the pulse beat intervals.

Due to the presence of a pulse deficit in atrial fibrillation, results based on ventricular contractions determined by the electrocardiogram may not apply to time intervals determined from analyzing the pulse. Furthermore, the extent of the pulse deficit depends on the method used to determine the pulse beats. A method which detects only pulse beats with high systolic pressures will detect fewer pulse beats compared to a more sensitive method. The more sensitive techniques may be better for detecting more pulse beats but they may also give more false positive readings.

For example, with a photoplethysmograph using a finger probe with a light source and a photoelectric detector, when the sensitivity of the device is increased, the slightest finger movement is detected as a pulse beat. This device at the highest sensitivity setting detects an irregular pulse in those with normal sinus rhythm due to random noise from finger movement. At the highest sensitivity setting, this device would not be useful to detect atrial fibrillation in the home setting. At the lowest sensitivity setting, very few pulse beats would even be detected. Therefore, any device and algorithm which uses the pulse to detect atrial fibrillation must be designed specifically for the purpose of detecting atrial fibrillation.

U.S. Pat. No. 6,095,984 describes an apparatus that can detect "arrhythmia" using the pulse wave. There is no mention of atrial fibrillation in their patent. In fact, the embodiments of their patent that they describe would detect any premature beat, which is a very common rhythm abnormality. Even the most common rhythm disturbance, sinus arrhythmia, which is considered to be a variant of the normal sinus rhythm, would be detected as an arrhythmia by an apparatus constructed in accordance with U.S. Pat. No. 6,095,984. Indeed, U.S. Pat. No. 6,095,984 describes an embodiment (section 1-2-1) where a pulse variation over 0.5% would be detected as abnormal. In sinus arrhythmia, by definition (Braunwald, E. Heart Disease A textbook of Cardiovascular Medicine 1992, p 674) the heart rate varies by more than 10%. U.S. Pat. No. 6,095,984 did not describe methods and apparatus to look for atrial fibrillation and would not be useful for home monitoring of atrial fibrillation, because the algorithm can result in multiple sources of false readings and the apparatus was not specifically set for optimal detection of pulse beats in atrial fibrillation.

An algorithm designed to detect atrial fibrillation by the irregularity of the pulse beat intervals should be designed to reduce the effects of premature beats. One method of reducing the effect of premature beats is to limit the number of beats used in determining the irregularity of the pulse intervals. For example, if premature beats occur on average every twenty beats, then limiting the analysis to only ten beats would reduce the likelihood of a premature beat occurring during the period being analyzed.

There are several devices available that measure both blood pressure and pulse rate, but none of these devices is capable of monitoring, detecting and/or communicating whether or not an irregular heartbeat pattern is present to indicate possible atrial fibrillation. The commercially available devices measure the number of pulse beats over a preset time interval, usually ten (10) seconds, but these devices neither analyze nor determine the presence of irregular heartbeat rhythms.

Commercially available automatic devices for simultaneously determining pulse rates and measuring the blood pressure are available. The most widely used of these devices use the oscillometric or the auscultatory method. In both methods a cuff is placed around an appendage such as an arm and inflated above the systolic blood pressure.

Oscillometry is based on the measurement of the change in the air pressure oscillations in the pressure cuff during cuff deflation. With the auscultatory method, the Karatkoff sounds are recorded when the cuff is deflated. Each of these methods can be used to measure both the blood pressure and to detect the pulse beats.

However, a pulse beat can only be detected by these devices when the systolic pressure of the beat exceeds a minimum value. This minimum value varies with the cuff pressure and the technique used to measure the pressure.

Using the oscillometric method, at higher cuff pressures only heart beats with higher systolic pressures will be detected. For example, a person in normal sinus rhythm with a systolic blood pressure of 120 mm Hg for each beat may have no pulses detected when the cuff pressure exceeds 200 mm Hg. This occurs since the amplitude of the oscillations in the cuff is minimal under these circumstances. However, the device will detect the pulses of another person with a systolic pressure of 180 mm Hg when the cuff is inflated to 200 mm Hg. For the person with a systolic blood pressure of 120 mm Hg, the device begins to detect pulses only when the cuff pressure is reduced well below 200 mm Hg. In this case, it may detect pulses when the cuff pressure is 150 mm Hg or below.

In atrial fibrillation, the time intervals between beats varies irregularly and the systolic pressure of each heart beat also varies. Therefore, when the cuff of these automatic sphygmomanometers is inflated to a high pressure it will only detect pulses with higher systolic pressures. As the cuff pressure is reduced, more pulses can then be detected since the pulses with lower systolic pressures as well as the higher systolic pressure pulses can then be detected. This unique variation in sensitivity to pulse beats means that an algorithm must be designed specifically to detect atrial fibrillation using the automatic blood pressure cuff.

In addition, someone with a normal rhythm may still have a change in his systolic blood pressure from one beat to the next due to the effects of normal respiration. Even though this variation in systolic pressures is usually less than 10 mm Hg, it may be enough to cause some normal sinus beats not to be detected when the blood pressure cuff is inflated to high pressures. Therefore, the algorithm for determining if the rhythm is regular must allow for potential irregular intervals that occur when the blood pressure cuff is inflated to a high pressure.

What is needed is a home monitoring method and apparatus to detect the possible presence of atrial fibrillation and communicate this condition to the user so that the user is alerted to consult a medical practitioner for further testing and/or treatment.

What is also needed is a method that can differentiate an irregular pulse rate pattern from a normal pulse rate pattern and from common heart rhythm patterns that are not of significant risk, such as regular sinus rhythm, sinus arrhythmia, atrial premature beats and ventricular premature beats.

What further is needed is a method of and an apparatus for detecting irregular pulse rhythms during a time period and storing this information so that comparisons may be made with the pulse rate rhythms at later times.

What is further needed is a noninvasive and relatively simple method and apparatus that monitors pulse rate irregularities to detect atrial fibrillation, and that is suitable for use of all ages, and by the hearing and/or visually impaired and that is relatively easy to use.

What is still further needed is a monitoring method and apparatus that detects the presence of irregular pulse beats and then displays and stores: i) the number of irregular pulse beats during a pre-selected time interval; and ii) the duration of time between beats during selected intervals.

Yet another need is for a monitoring method and apparatus that determine whether or not a pulse beat pattern is irregular based on algorithmic or heuristic operations performed on selected pulse beat data.

What is needed is a method and apparatus for detecting the presence of atrial fibrillation by detecting an irregular pattern of pulses using a sphygmomanometer.

What is needed is a method and apparatus for detecting the presence of atrial fibrillation by detecting an irregular pattern of pulses using a plethysmograph such as finger probe with a light source and photodetector.

BRIEF SUMMARY OF THE INVENTION

The present invention provides a method and apparatus that determines the presence of atrial fibrillation (i) by detecting the pulse beat intervals over a short time period to determine whether the intervals form a random, irregular pattern (ii) determines whether this pulse beat pattern indicates possible atrial fibrillation and then (iii) communicates this information to the user so that a medical practitioner may be consulted for further testing and/or treatment. The present invention also provides a method of and an apparatus for detecting irregular pulse rhythms during a time period and storing this information for comparison with the pulse rhythm at later time periods. The present invention may also detect patterns over multiple time periods and compare the patterns over various time periods.

The present invention further provides a noninvasive method of and an apparatus for monitoring the irregularity of the pulse beat pattern to detect atrial fibrillation. The invention may store and display information such as the number of irregular pulse beats during pre-selected time intervals and the duration of time between beats during the selected intervals. The invention also determines the presence of an irregular pulse beat pattern via algorithmic or heuristic operations performed on the relevant data.

Pulse beats may be monitored by use of an inflatable cuff wrapped around a person's appendage, such as an arm, which detects the pulse beats by either oscillometric or auscultatory means. The time intervals between pulse beats can be determined during cuff deflation or while the cuff is inflated at a fixed pressure.

The present invention allows for the elimination of at least one or more of the initial pulse beat intervals detected during deflation of a blood pressure cuff. This is necessary due to the respiratory variation in the systolic pressure of sinus beats even in normal individuals.

Pulse beats may also be monitored through changes in light transmitted through various body appendages. Each pulse beat changes the light transmission through a location on the appendage. The change in the light transmission corresponds to a pulse beat and the time intervals between pulse beats may be determined.

Pulse beats may be monitored using other plethysmographic devices, ultrasound devices which measure arterial motion with each pulse beat, ultrasound doppler devices which detect blood flow within an artery or devices that rely on localized compression of the artery to detect the presence of a pulse beat. Using any of these techniques the time intervals between pulse beats can be determined.

A monitoring method of the present invention includes detecting irregular pulse beats, analyzing the irregularity based on one or more predetermined factors, and communicating this information to a user such as via a screen display, a paper printout, a tone, or auditory, vibratory or other sensory communication.

The invention may utilize algorithmic or heuristic techniques to determine whether the irregular pulse beats signal the possible presence of atrial fibrillation.

Other features and advantages of the present invention will become apparent from the following detailed description of the invention with reference to the accompanying drawings.

BRIEF DESCRIPTION OF THE DRAWINGS

The invention will now be described in greater detail in the following detailed description with the reference to the drawings in which.

DETAILED DESCRIPTION OF THE INVENTION

Figure 1:
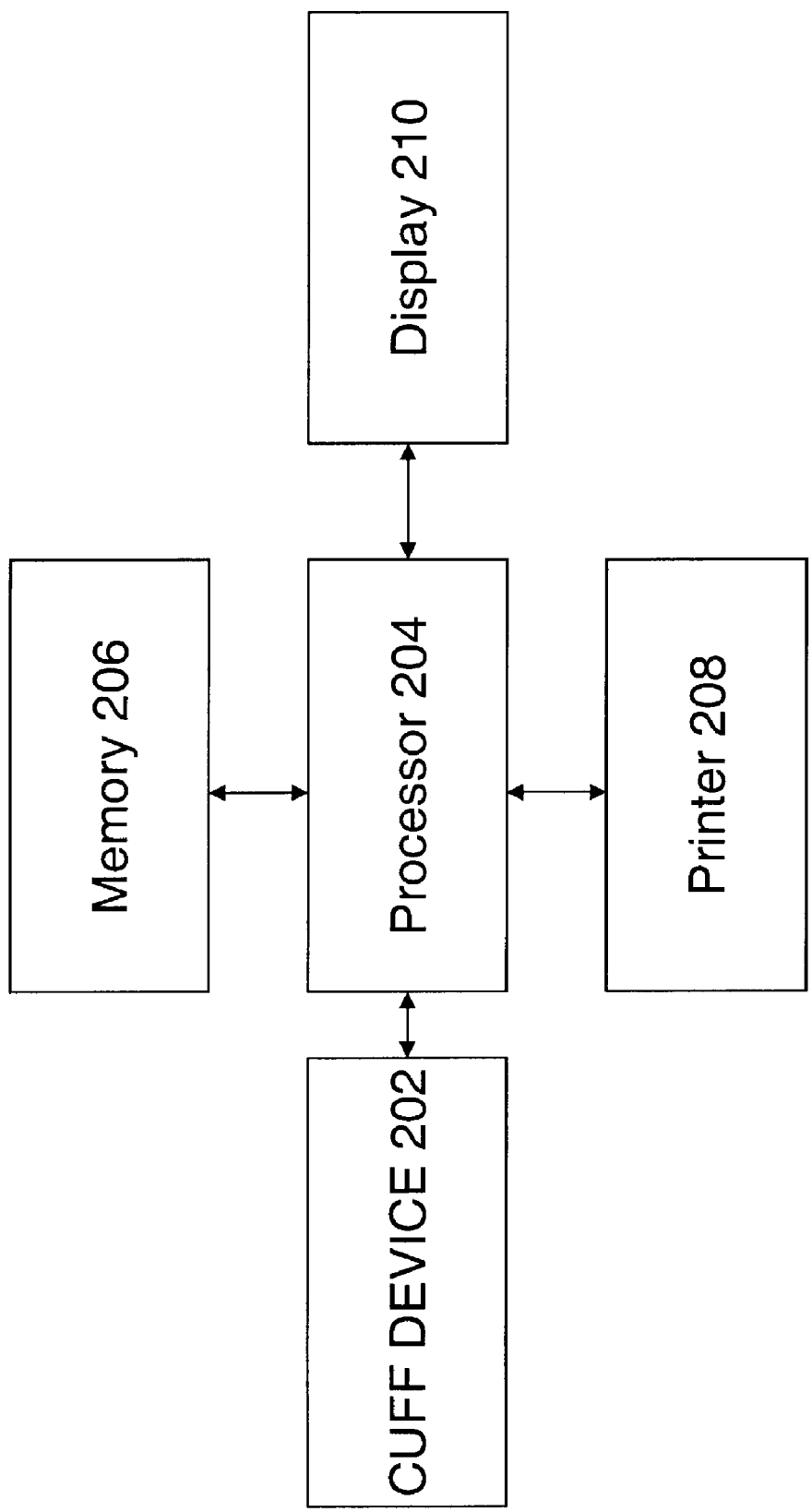
FIG. 1 is a block diagram showing an arrangement for detecting possible atrial fibrillation using an inflated cuff in accordance with the invention.

FIG. 1 shows an embodiment of the invention in which pulse beats are detected using an inflatable cuff device 202. The inflatable cuff device 202 may be a known apparatus used to measure blood pressure using oscillometric or auscultatory means.

The inflatable cuff device 202 is placed around an appendage such as an arm and inflated above systolic pressure. While the cuff is deflated, the pulse beats are detected. The cuff deflation may be stopped and the cuff may remain at a fixed pressure to allow for monitoring of the pulse beats during a constant cuff pressure. The time of each pulse beat is delivered to a processor 204, which includes instructions that carry out the method described above.

Further, the processor 204 stores the time of each pulse beat, the intervals between pulse beats and other information in a memory 206. The memory 206 may include RAM or other device memory or include a hard disc, a floppy disk or other memory devices. The processor 204 may comprise a microprocessor, and applications specific integrated circuit (ASIC), a programmable logic array (PLA) or reduced instruction set chip (RISC).

The processor eliminates at least the first interval detected at the start of the blood pressure cuff deflation. The processor 204 determines from the remaining pulse beat intervals if the pattern is regular or irregular. The processor then delivers the results to a printer 208 a display 210 a vibration generator, and/or an auditory generator, etc. which may include an indication that the pulse beat pattern is regular, irregular, in possible atrial fibrillation, or that a physician should be contacted. Other information, such as the pulse rate, may also be displayed.

This embodiment with an automatic sphygmomanometer that uses the oscillometric method for detecting the pulse beats and blood pressure was developed. To account for the pulse deficit at higher cuff pressures, and to account for possible respiratory variation in the systolic pressures of normal beats, and to reduce the influence of premature beats, an algorithm was developed that analyzed only the last ten beats detected during cuff deflation. The mean and standard deviation of these last ten beats was calculated and the quotient of the standard deviation over the mean was determined.

This was compared to a threshold value of 0.06. If the quotient was greater than the threshold value then the pulse pattern was determined to be irregular. To further reduce the possibility of occasional premature beats causing an irregular reading, the procedure was repeated a second time. A patient was considered to have an irregular rhythm if both trials showed an irregular pulse pattern. This device was applied to 203 ambulatory outpatients in a general cardiology practice with both atrial fibrillation and non-atrial fibrillation rhythms. Using this algorithm all 24 patients with atrial fibrillation were classified as having an irregular rhythm and 10 out of 179 non-atrial fibrillation patients were classified as having an irregular rhythm. This resulted in a sensitivity of detecting atrial fibrillation of 100% and a specificity of 94%. Thus, with an appropriate algorithm, this method can detect atrial fibrillation with a high degree of accuracy.

Figure 2:
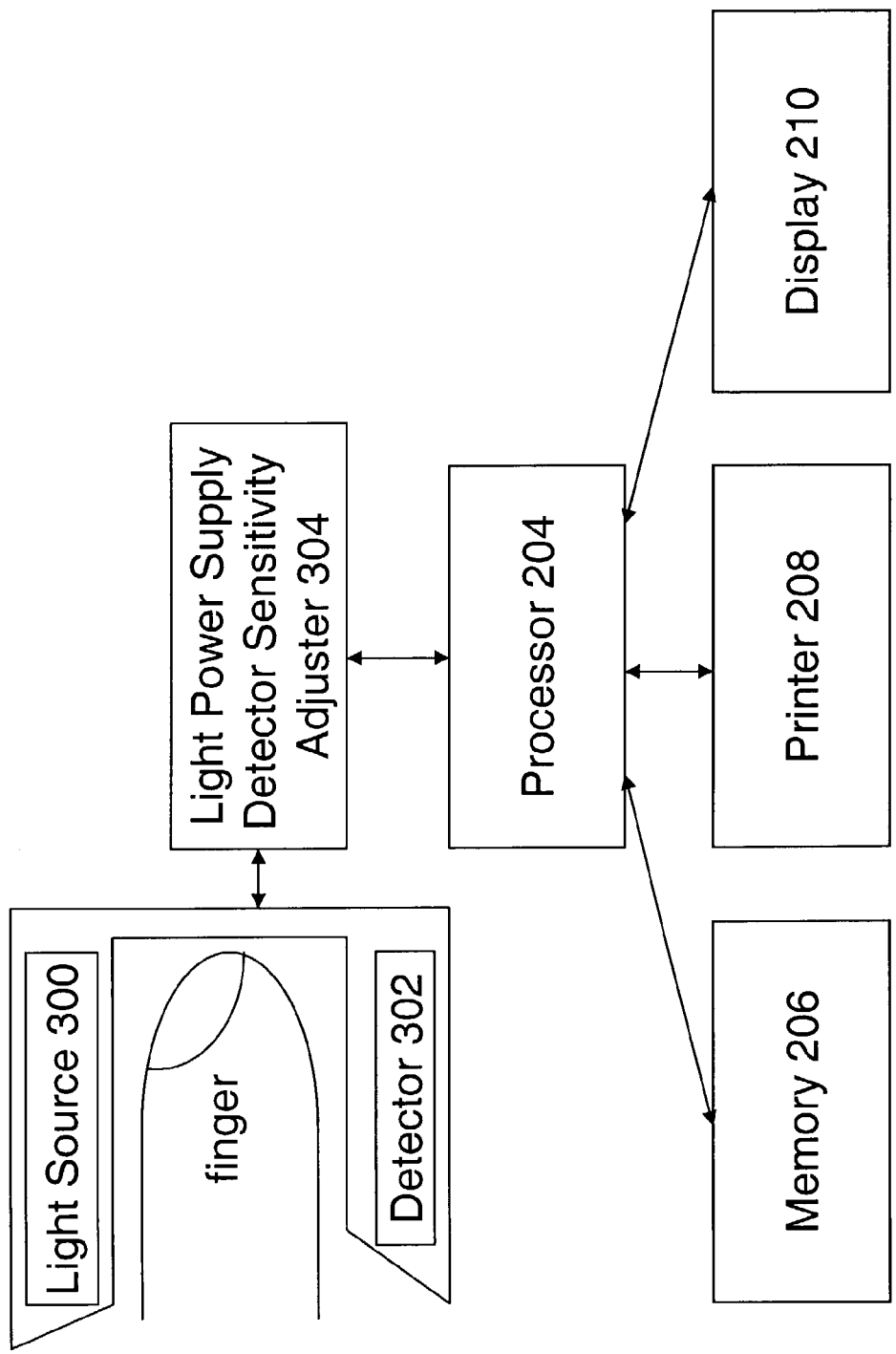
FIG. 2 is a schematic diagram showing an arrangement for detecting possible atrial fibrillation by detecting changes in the amount of blood that is absorbed in an appendage area such as a finger.

FIG. 2 shows another embodiment of the invention in which the pulse rate is monitored through changes in light transmitted through a body appendage, such as a finger.

Light is transmitted by a light source 300 through the finger, or other appendage of an individual, and is received by a detector 302, which measures the change in light transmitted through the appendage to detect a pulse beat. The detector 302 may comprise a conventional pulse measurement device. The detector 302 delivers the time of each measured pulse to the processor 204, which carries out the operations described above regarding FIG. 1. As depicted in FIG. 2, a light power supply detector sensitivity adjuster 304 may be used to adjust the sensitivity of the detector in a known manner with respect to detecting the light from the light source. To detect the pulse beat, the finger or other appendage is placed between the light source and the detector and the light source is activated to shine light through the finger to reach the detector.

Advantageously, the invention provides a method and apparatus that easily detect the presence of irregular heartbeats from a plurality of heartbeats, pulses or other measurements.

As a further advantage, the invention differentiates a normal heartbeat pattern from an irregular heartbeat pattern.

A still further advantage is that the invention provides relatively simple, non-invasive home monitoring.

Although the present invention has been described in relation to particular embodiments thereof, many other variations and modifications and other uses may become apparent to those skilled in the art. It is preferred, therefore, that the present invention be limited not by this specific disclosure herein, but only by the appended claims.

What is claimed is:

1. A method of determining possible atrial fibrillation, said method comprising the steps of:
   (a) detecting irregular pulse rhythms from a succession of time intervals each corresponding to a respective interval of time between successive pulse beats of a sequence of the pulse beats;
   (b) analyzing the detected irregular pulse rhythms to make a determination of possible atrial fibrillation; and
   (c) indicating the possible atrial fibrillation from the determination.

2. A method of claim 1, wherein the analyzing includes ascertaining a mean and a standard deviation of the succession of time intervals, the determination being based upon a quotient formed by dividing said standard deviation by said mean and comparing the quotient with a threshold value.

3. A method of claim 2, wherein the determination includes determining that the sequence of the pulse beats is irregular in response to the quotient being greater than or equal to the threshold value.

4. The method of claim 2, wherein the determination includes determining that the sequence of the pulse beats is regular in response to the quotient being less than the threshold value.

5. The method of claim 1, wherein the detecting of the irregular pulse rhythms is with an inflatable cuff, and configuring the inflatable cuff to monitor the pulse rates to thereby detect the irregular pulse rhythms.

6. The apparatus of claim 5, wherein the inflatable cuff includes a sphygmomanometer.

7. The method of claim 1, wherein the detecting of the irregular pulse rhythms is by monitoring changes in light transmitted through a body appendage of the individual.

8. The method of claim 2, further comprising the step of storing at least one of said plurality of time intervals, said mean, said standard deviation, said quotient and said threshold value.

9. The method of claim 2 wherein said threshold value is within the range of 0.05 to 0.10.

10. The method of claim 1, wherein the indicating includes outputting an indication that is indicative of the possible atrial fibrillation by outputting to a device selected from a group consisting of a printer, a display, an auditory signal generator and a vibration signal generator.

11. A method as in claim 1, further comprising:
    detecting a plurality of pulse beats including the sequence of pulse beats using a sphygmomanometer; and
    compensating for respiratory variation in systolic pressure of the pulse beats by designating the succession of time intervals to exclude at least an initial one of the plurality of time intervals.

12. An apparatus for determining possible atrial fibrillation, comprising:
    a detector configured to detect irregular pulse rhythms from a succession of time intervals each corresponding to a respective interval of time between successive pulse beats of a sequence of the pulse beats;
    a processor configured to analyze the detected irregular pulse rhythms for making a determination of possible atrial fibrillation; and
    an indicator configured to indicate the possible atrial fibrillation based on the determination.

13. An apparatus of claim 12, wherein the processor is configured to ascertain a mean and a standard deviation of the succession of the time intervals, the processor being configured to analyze the detected irregular pulse rhythms for possible atrial fibrillation based upon a quotient formed by dividing said standard deviation by said mean and comparing the quotient with a threshold value.

14. The apparatus of claim 12, wherein said detector includes an inflatable-cuff device.

15. The apparatus of claim 14, wherein the detector includes a sphygmomanometer.

16. The apparatus of claim 12, wherein said detector is configured to detect changes in light transmitted through an appendage of an individual.

17. The apparatus of claim 12, wherein said indicator includes an output device selected from a group consisting of a printer, a display, an auditory signal generator, and a vibration signal generator, the output device being configured to output an indication indicative of the possible atrial fibrillation.

18. The apparatus of claim 12, wherein said processor comprises at least one of a microprocessor, and application specific integrated circuit (ASIC), a programmable logic array (PLA) and a reduced instruction set chip (RISC).

19. The apparatus of claim 13, wherein said processor determines irregular cardiac activity in response to the quotient being greater than or equal to the threshold value.

20. The apparatus of claim 13, wherein said processor determines regular, normal cardiac activity in response to the quotient being less than the threshold value.

21. The apparatus of claim 13, wherein said threshold value is within the range of 0.05 to 0.10.

22. The apparatus as in claim 12, further comprising a sphygmomanometer that has a detector configured to detect a plurality of the pulse beats including the sequence of pulse beats; and
    a compensator configured to compensate for respiratory variation in systolic pressure of the pulse beats by designating the succession of time intervals to exclude at least an initial one of the plurality of time intervals.

* * * * *